(12) United States Patent
Chan et al.

(10) Patent No.: US 10,105,306 B2
(45) Date of Patent: Oct. 23, 2018

(54) METHOD OF PREPARING A GROWTH FACTOR CONCENTRATE

(71) Applicant: Bestop Group Holdings Limited, Hong Kong (HK)

(72) Inventors: Kin Yip Chan, Hong Kong (HK); Wing Man Tam, Hong Kong (HK)

(73) Assignee: Bestop Group Holdings Limited, Hong Kong (HK)

( * ) Notice: Subject to any disclaimer, the term of this patent is extended or adjusted under 35 U.S.C. 154(b) by 0 days.

(21) Appl. No.: 15/436,890

(22) Filed: Feb. 20, 2017

(65) Prior Publication Data

US 2017/0157018 A1     Jun. 8, 2017

Related U.S. Application Data

(63) Continuation-in-part of application No. 14/487,113, filed on Sep. 16, 2014, now abandoned.

(30) Foreign Application Priority Data

Sep. 17, 2013 (HK) .................................. 13110684

(51) Int. Cl.
| | | |
|---|---|---|
| *A61K 38/18* | (2006.01) | |
| *A61K 35/16* | (2015.01) | |
| *A61K 35/19* | (2015.01) | |
| *A61K 8/64* | (2006.01) | |
| *A61Q 19/08* | (2006.01) | |
| *A61N 1/04* | (2006.01) | |
| *A61K 8/98* | (2006.01) | |

(52) U.S. Cl.
CPC ................ *A61K 8/64* (2013.01); *A61K 8/983* (2013.01); *A61K 35/16* (2013.01); *A61K 35/19* (2013.01); *A61K 38/18* (2013.01); *A61K 38/1808* (2013.01); *A61K 38/1825* (2013.01); *A61K 38/1833* (2013.01); *A61K 38/1858* (2013.01); *A61K 38/1866* (2013.01); *A61K 38/1875* (2013.01); *A61N 1/0408* (2013.01); *A61Q 19/08* (2013.01); *A61K 2800/84* (2013.01)

(58) Field of Classification Search
None
See application file for complete search history.

(56) References Cited

U.S. PATENT DOCUMENTS

| | | | |
|---|---|---|---|
| 7,776,342 B2 * | 8/2010 | Fernandez Molina | A61K 39/0011 424/184.1 |
| 2013/0030161 A1 * | 1/2013 | Anitua Aldecoa | A61K 38/18 530/399 |
| 2015/0224173 A1 * | 8/2015 | Totey | A61K 38/1858 424/141.1 |

FOREIGN PATENT DOCUMENTS

WO    WO2016196515    * 12/2016    ............. A61P 17/02

* cited by examiner

*Primary Examiner* — Elly-Gerald Stoica

(57) ABSTRACT

Provided herein are growth factor concentrates, the method of preparing the growth factor concentrates, cosmetic compositions and methods for cosmetic treatment. The growth factor concentrates include decapsulated growth factors derived from platelet rich plasma.

8 Claims, 4 Drawing Sheets

METHOD OF PREPARING A GROWTH FACTOR CONCENTRATE

CROSS REFERENCE TO RELATED APPLICATIONS

This application is a continuation-in-part of U.S. patent application Ser. No. 14/487,113, filed on Sep. 16, 2014, which claims the benefit of Hong Kong Short-term Patent Application No. 13110684.5 filed on Sep. 17, 2013, the entire contents of which are incorporated herein by reference.

FIELD OF INVENTION

This invention relates to a growth factor concentrate and the use thereof, in particular the use in cosmetic treatment.

BACKGROUND OF INVENTION

Growth factors are a group of naturally occurring proteins or steroid hormones that are capable of stimulating cellular growth, proliferation and cellular differentiation. Growth factors are important for regulating a variety of cellular processes and play an important part in maintaining healthy skin structure and function.

Some types of cells, such as keratinocytes making up the epidermis and dermis of the skin can secret growth factors. However, the concentration of growth factor may be decreased age-relatedly. Since the skin should be fertilized by growth factors theoretically, some cosmetic products or cosmetic treatments nowadays are applying growth factors on the surface of the skin, in which the growth factors are extracted from the subject in need thereof. The cosmetic effects which are expected by applying growth factors on the skin surface include but not limited to: reducing the fine lines, expression lines and wrinkles as a result of new collagen synthesis; reducing the dark spots and pigmentation; improving the density, smoothness and firmness; and reducing the uneven skin texture and tone.

Platelet rich plasma (PRP) extracted from the subject in need thereof is used for growth factor treatment. However, the PRP must be used freshly, and cannot be stored for a long period of time. The average life span of platelets is typically only 5 to 9 days after extraction. In skin-care products, growth factors would be used repeatedly, and possibly over long periods of time. A normal cosmetic treatment of growth factors requires several times of treatments spanning a period of 3 to 6 months. Typically, every time before receiving treatment, the subject in need thereof has to suffer venipuncture and wait for at least 30 minutes for the PRP to be extracted. Some products use additives such as preservative or other chemical to extend the shelf life of growth factors.

Moreover, the absorption of the applied growth factors on the skin surface may not be as well as expected because of the block of epidermis. In addition, the PRP treatment known in the art does increase the number of platelets surrounding skin cells, but only a small amount of growth factors can be released from platelets at a slow rate.

It is necessary to provide no-additive and stable growth factors self-provided by the subject in need with a high released concentration and a longer shelf life.

SUMMARY OF INVENTION

In the light of the foregoing background, it is an object of the present invention to provide a growth factor concentrate for cosmetic treatment to a subject in need thereof, in which the growth factor concentrate comprises decapsulated growth factors derived from platelet rich plasma.

In an exemplary embodiment of the present invention, the platelet rich plasma is extracted from the subject.

In another exemplary embodiment of the present invention, the growth factor concentrate is preserved by steps of:
a. extracting a whole blood sample from the subject, wherein the platelet rich plasma with the growth factors are contained therein;
b. obtaining the platelet rich plasma from the blood sample;
c. stabilizing the platelet rich plasma;
d. decapsulating the growth factors of the stabilized platelet rich plasma;
e. filtering out the decapsulated growth factors;
f. freeze-drying the filtered growth factors to obtain the growth factor concentrate; and
g. preserving the freeze-dried growth factor concentrate.

The growth factor concentrate is preserved for an extended period of time.

In a further exemplary embodiment of the present invention, the decapsulating step further comprises the step of freezing and thawing the platelet rich plasma. In another exemplary embodiment, the platelet rich plasma is frozen at a temperature between $-50°$ C. and $-60°$ C. for at least 30 minutes; in yet another exemplary embodiment, the platelet rich plasma is thawed at a temperature of $37°$ C. for 10 minutes. In one exemplary embodiment, the decapsulated growth factors are filtered through a cellulose acetate membrane in the filtering step. In yet another exemplary embodiment, the freezedrying step further comprises the steps of:
f1. freezing the filtered growth factors at a temperature between $-50°$ C. and $-60°$ C. for at least 3°hours; and f2. lyophilizing the frozen growth factors at a temperature between $-40°$ C. and $-60°$ C. and at a pressure of about 0.18 millibar for at least 10 hours. In another exemplary embodiment, the freeze-dried growth factor concentrate is preserved at a temperature ranging from $2°$ C. to $10°$ C. in the preserving step.

In another exemplary embodiment of the present invention, the growth factor concentrate is a cryo-crystalized growth factor concentrate.

In yet another exemplary embodiment of the present invention, the growth factor concentrate has a shelf life of at least 22 months.

According to another aspect of the present invention, an anti-aging cosmetic composition for a subject in need thereof is provided, in which the anti-aging cosmetic composition comprises an effective amount of the growth factor concentrate as described above.

Therefore, in yet another exemplary embodiment of the present invention, the growth factor concentrate is prepared by a method comprising the steps of:
extracting a whole blood sample from a subject, wherein platelet rich plasma with the growth factors are contained therein;
obtaining the platelet rich plasma from the blood sample;
stabilizing the platelet rich plasma by adding a Tris Buffer at 2% in volume to stabilize pH at 7 to avoid undesired fluctuations of pH value in temperature extremes of the following steps;
decapsulating the growth factors from the platelets of the stabilized platelet rich plasma comprising: 1) lysing the stabilized platelet rich plasma with a lysing solution containing an anticoagulant; and 2) freezing the platelet rich plasma at a temperature between $-50°$ C. and $-60°$ C.

for 5-30 minutes and thawing the platelet rich plasma at a temperature of 37° C. for 10-30 minutes;

filtering out the decapsulated growth factors by a 0.2 μm cellulose acetate membrane;

freeze-drying the filtered growth factors by freezing the filtered growth factors at a temperature between −50° C. and −60° C. for at least 3 hours and lyophilizing the frozen growth factors at a temperature between −40° C. and −60° C. and at a pressure of about 0.01-0.18 millibar for at least 10 hours, wherein the freeze-dried growth factor concentrate has humidity of lower than 70%; and preserving the freeze-dried growth factor concentrate at about 4° C.

Therefore, in yet another exemplary embodiment, of the present invention, the growth factor concentrate is prepared by a method comprising the steps of:

extracting a whole blood sample from a subject, wherein platelet rich plasma with the growth factors are contained therein;

obtaining the platelet rich plasma from the blood sample;

decapsulating and stabilizing the growth factors from the platelets rich plasma comprising: 1) lysing the platelet rich plasma with a lysing solution containing an anticoagulant; 2) stabilizing the platelet rich plasma by adding a Tris Buffer at 2% in volume to stabilize pH at 7 to avoid undesired fluctuations of pH value in temperature extremes of the following steps; and 3) freezing the platelet rich plasma at a temperature between −50° C. and −60° C. for 5-30 minutes and thawing the platelet rich plasma at a temperature of 37° C. for 10-30 minutes;

filtering out the decapsulated growth factors by a 0.2 μm cellulose acetate membrane;

freeze-drying the filtered growth factors by freezing the filtered growth factors at a temperature between −50° C. and −60° C. for at least 3 hours and lyophilizing the frozen growth factors at a temperature between −40° C. and −60° C. and at a pressure of about 0.01-0.18 millibar for at least 10 hours, wherein the freeze-dried growth factor concentrate has humidity of lower than 70%; and preserving the freeze-dried growth factor concentrate at about 4° C.

In another aspect of the present invention, a non-invasive method for promoting skin rejuvenation in a subject in need thereof is provided, in which the method comprises topically applying a cosmetic composition comprising an effective amount of the growth factor concentrate as described above.

In a further aspect of the present invention, a method for rejuvenating the skin of a subject in need thereof is provided, in which the method comprises the steps of:

a. cleaning the target area of the skin of the subject;

b. applying a probe from a device generating radio frequency on the cleaned skin to create channels within the cleaned skin; and c. applying a cosmetic composition comprising an effective amount of the growth factor concentrate on the cleaned skin from step b such that the cosmetic composition can penetrate into deeper layers of the cleaned skin through the channels.

DETAILED DESCRIPTION OF THE PREFERRED EMBODIMENTS

Figure 1:
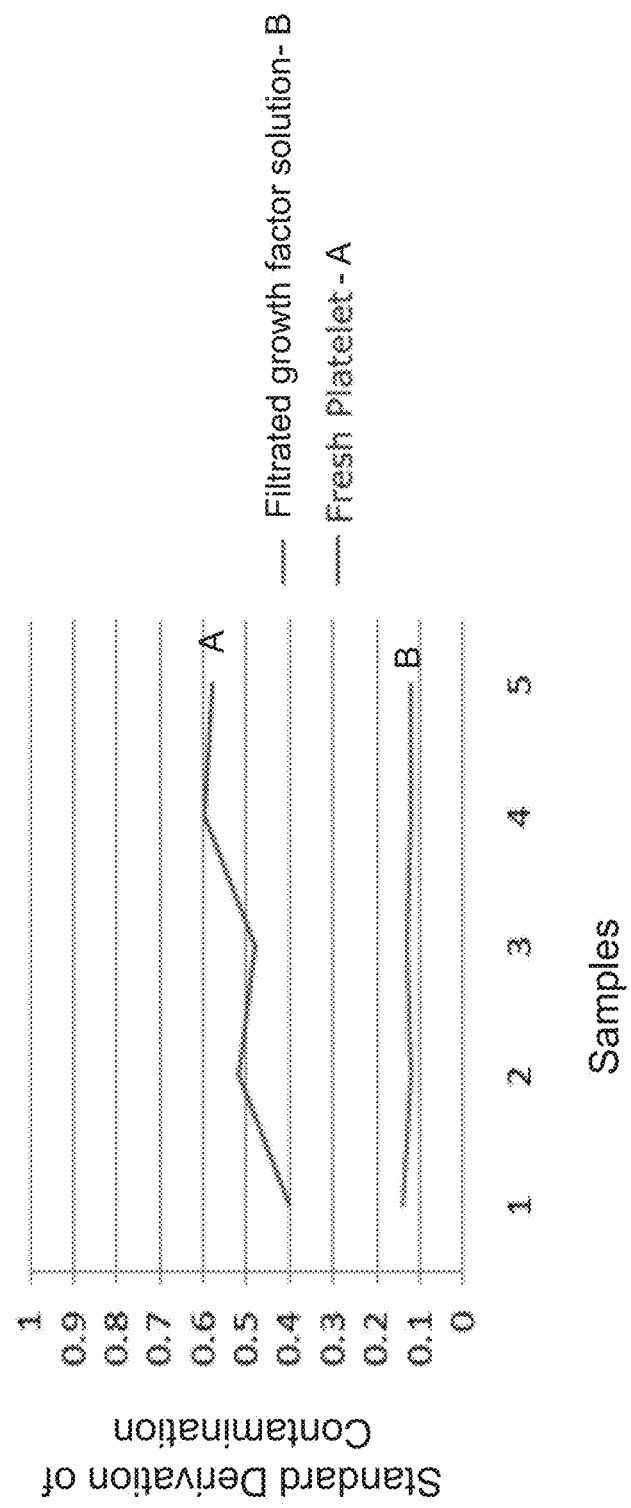
FIG. 1 shows the standard derivation of contamination of the extracted growth factor concentrate and fresh platelet in a study on the safety of the growth factor concentrate provided in the present invention.

As used herein and in the claims, "comprising" means including the following elements but not excluding others.

Preparation of Growth Factor Concentrate

1. Collecting PRP 30 ml-60 ml whole blood sample was extracted from the subject by venipuncture or any other suitable means and stored in a sodium citrate blood collection tube or any other suitable containers for ease of transport.

The PRP layer was separated from blood cell layer by centrifuge at 3000 rpm or any other suitable means. The growth factors are now concentrated in the separated PRP solution.

2. Stabilizing PRP Layer

A buffering agent was added to the separated PRP layer (a.k.a "the PRP solution") to stabilize the pH value of PRP within a desired range to avoid undesired fluctuations of pH value in temperature extremities. Such undesired fluctuations of pH value may affect the efficacy of growth factors in the following steps including temperature change.

The buffering agent that could be added to the PRP solution as a lyoprotectant is Tris Buffer. In one embodiment, about 2% in volume of 0.5 M Tris Buffer is added to the PRP solution and the resultant pH value of the PRP solution is 7.

3. Decapsulating Growth Factor

Platelets are prone to apoptosis at low storing temperature which may release inhibitors and destroy the growth factors therein. Besides, as mentioned above, absorption rate of growth factors by the skin cell may be low, since only a small amount of growth factors are released from the platelets during the treatment. In the course of invention, the inventors intended to decapsulate the growth factors from platelets as the decapsulated growth factors tend to be less vulnerable to inhibitors and easier to be absorbed by the skin cell.

There are several methods that could release (decapsulate) growth factors from platelets, including but not limited to freezing-thawing, mechanical lysis, liquid homogenization, sonication and manual grinding. Freezing-thawing method is employed in one embodiment to decapsulate growth factors from the stabilized PRP solution.

In one embodiment, prior to freezing and thawing the growth factor in the PRP solution, a lysing solution containing an anticoagulant is added to the stabilized PRP solution. In one embodiment, the lysing solution contains an anticoagulant selected from the group consisting of heparin, warfarin, coumarin, dabigatran, rivarosaban, apixaban, edoxaban, sodium citrate and sodium calcium. In one embodiment, the anticoagulant is heparin. In one embodiment, the lysing solution is a NP-40 lysis buffer. In one embodiment, the NP-40 lysis buffer contains 50 mM Tris, pH 7.4, 250 mM NaCl, 5 mM Heprine, 50 mM NaF, 1 mM $Na_3VO_4$, 1% Nonidet P40, 0.02% $NaN_3$. In one embodiment, the lysing solution is a RIPA lysis buffer. In one embodiment, the RIPA buffer contains 1% (w/w) Nonidet P-40 (NP-40), 1% (w/v) sodium deoxycholate, 0.1% (w/v) SDS, 0.15 M NaCl, 0.01 M sodium phosphate, pH 7.2, 2 mM EDTA, 50 mM sodium fluoride (NaF), 0.2 mM fresh sodium orthovanadate ($Na_3VO_4.2H_2O$, it has phosphatase inhibitor function because it mimics phosphate[9]), 100 U/ml protease inhibitor, such as aprotinin.

Optionally the lyoprotectant described above could be added to the growth factor in the PRP layer following the addition of the lysing solution and anticoagulant described herein.

The stabilized PRP solution was frozen at a temperature of −50° C. to −60° C. for 5-30 minutes, preferably for 5 minutes, 10 minutes, 15 minutes, 20 minutes, or 30 minutes and then thawed in water bath at 37° C. for 10-30 minutes, preferably for 10 minutes, 15 minutes, 20 minutes, 25 minutes, or 30 minutes. The above freezing-thawing cycle was repeated for 3 more times. By way of freezing and thawing the aforesaid ice crystal formation in the platelets expands in volume and eventually ruptures the platelet membrane; thus growth factors are released from platelets and a decapsulated growth factor solution is then obtained.

By decapsulating the growth factors from platelets, the preservation period of growth factors can be much extended and the absorption rate can also be increased.

4. Filtrating the Decapsulated Growth Factor

To reduce the amount of pathogens and other contaminants such as bacteria, red blood cells or cell fragments which may affect the sterility of the solution and the life span of the growth factors, the decapsulated growth factor solution was filtrated by a 0.2 μm cellulose acetate membrane. As shown in FIG. 1, filtrated growth factor solution clearly has a lower standard derivation of contamination under the same condition than that of fresh platelet, showing that filtrated growth factor solution is safer than fresh platelet.

The filtrated growth factor solution was then distributed into serum vials that were sealed with rubber stoppers and frozen. In one embodiment, these vials were frozen at a temperature between −50° C. and −60° C. for at least 3 hours to prepare for freeze-drying.

5. Freeze-drying

Freeze-drying, also known as cryodesiccation, works by freezing the material and then reducing the surrounding pressure to allow the frozen water in the material to sublimate directly from the solid phase to the gas phase. This method has been used in preserving perishable material or making the material more convenient for transport.

The vials containing the filtrated growth factor solution were retrieved from storage; in one embodiment of the present invention, the storage temperature was −55° C. The loosely covered vials were then put into a freeze-dryer. In one embodiment, the freeze-drying process was maintained at a temperature between −40° C. and −60° C. and at a pressure of about 0.01-0.18 millibar, for at least ten hours until samples of growth factors were dried thoroughly. The growth factor concentrate was obtained in a form of powder (also known as cryo-crystalized growth factor, C-GF).

6. Storing

Upon visual inspection of the vials for sufficient dryness of the powder, the vials were resealed, sealed air-tight and removed from the freeze-dryer to a temperature, in one embodiment, of 2° C.-10° C. with humidity of lower than 70%, which can be stored up to six months. In another embodiment of the present invention, the growth factor concentrate prepared from the aforesaid steps and stored in a typical household refrigerator may then have shelf life as long as 22 months.

Therefore, in one embodiment, the present invention provides a method of preparing growth factor concentrate comprising the steps of:
extracting a whole blood sample from a subject, wherein platelet rich plasma with the growth factors are contained therein;
obtaining the platelet rich plasma from the blood sample;
stabilizing the platelet rich plasma by adding a Tris Buffer at 2% in volume to stabilize pH at 7 to avoid undesired fluctuations of pH value in temperature extremes of the following steps;
decapsulating the growth factors from the platelets of the stabilized platelet rich plasma comprising: 1) lysing the stabilized platelet rich plasma with a lysing solution containing an anticoagulant; and 2) freezing the platelet rich plasma at a temperature between −50° C. and −60° C. for 5-30 minutes and thawing the platelet rich plasma at a temperature of 37° C. for 10-30 minutes;
filtering out the decapsulated growth factors by a 0.2 μm cellulose acetate membrane;
freeze-drying the filtered growth factors by freezing the filtered growth factors at a temperature between −50° C. and −60° C. for at least 3 hours and lyophilizing the frozen growth factors at a temperature between −40° C. and −60° C. and at a pressure of about 0.01-0.18 millibar for at least 10 hours, wherein the freeze-dried growth factor concentrate has humidity of lower than 70%; and
preserving the freeze-dried growth factor concentrate at about 4° C.

Therefore, in one embodiment, the present invention provides a method of preparing growth factor concentrate comprising the steps of:
extracting a whole blood sample from a subject, wherein platelet rich plasma with the growth factors are contained therein;
obtaining the platelet rich plasma from the blood sample;
decapsulating and stabilizing the growth factors from the platelets rich plasma comprising: 1) lysing the platelet rich plasma with a lysing solution containing an anticoagulant; 2) stabilizing the platelet rich plasma by adding a Tris Buffer at 2% in volume to stabilize pH at 7 to avoid undesired fluctuations of pH value in temperature extremes of the following steps; and 3) freezing the platelet rich plasma at a temperature between −50° C. and −60° C. for 5-30 minutes and thawing the platelet rich plasma at a temperature of 37° C. for 10-30 minutes;
filtering out the decapsulated growth factors by a 0.2 μm cellulose acetate membrane;
freeze-drying the filtered growth factors by freezing the filtered growth factors at a temperature between −50° C. and −60° C. for at least 3 hours and lyophilizing the frozen growth factors at a temperature between −40° C. and −60° C. and at a pressure of about 0.01-0.18 millibar for at least 10 hours, wherein the freeze-dried growth factor concentrate has humidity of lower than 70%; and preserving the freeze-dried growth factor concentrate at about 4° C.

Compositions Containing the Growth Factor Concentrate

In another aspect, the present invention provides a composition having growth factor concentrate of the present invention described herein. In one embodiment, the concentration of the growth factor concentrate is from about 1 weight percent (wt. %) to about 50 wt. %, or from about 1 wt. % to about 20 wt. %, or about 5 wt. %, or about 10 wt. %, or about 20 wt. %, or about 30 wt. %, or about 40 wt. %, or about 50 wt. %.

In one embodiment, the composition described herein is for topical administration to a subject.

In one embodiment, the composition is a cosmetic composition containing the growth factor concentrate and a carrier. The carrier may be one or more conventional cosmetic adjuvants, such as additional fat or lipid substances, organic solvents, thickeners, binders, conditioning agents (e.g., hydrocarbon oils, fatty esters, silicones), demulcents, opacifiers, stabilizers, buffering agents, humectants, pigments, dyes, viscosity modifiers, emollients, antiperspirants, anti-foaming agents, foam boosters, hair colorants, hair perming agents, hair growth or restorer agents, hair loss prevention agents, abrasives, absorbents, anti-acne agents, anti-caking agents, moisturizing agents, perfumes or fragrances, preservatives, sunscreens, astringents, propellants, bleaching or lightening agents for skin or hair, tanning agents, deposition aids, suspending agents, polymers, fillers, sequestrants, bactericides and/or odor absorbers, antifungal agents, alkalinizing or acidifying agents, pearlescent aids, chelants, proteins, anti-dandruff agents, surfactants, emulsifiers, anti-free radical agents, antioxidants, vitamins (e.g., vitamins A, B1, B2, B6, B12, C, D, E, etc. and their derivatives), .alpha.-hydroxy acids, or any other ingredient normally used in cosmetics. Commonly used natural and synthetic adjuvants are described, for example, in Breslawec, Halyna P., and Tara E. Gottschalck. International Cosmetic Ingredient Dictionary and Handbook. Washington, D.C.: Personal Care Products Council, 2012, (hereinafter "Cosmetic Handbook") and Personal Care Products Council (formerly the Cosmetic, Toiletry and Fragrance Association or CTFA) ingredient information (see http://www.personalcarecouncil.org/public-information/consumer-ingredient-information), the content of which is hereby incorporated by reference in its entirety.

In one embodiment, the composition or the cosmetic composition of the present invention may take the form of a cream, a lotion, an ointment, a hydrogel, a colloid, a gel, a foam, an oil, a milk, a suspension, a wipe, a sponge, a solution, an emulsion, a paste, a patch, a pladget, a swab, a dressing, a spray or a pad.

Administering the End Product with Growth Factor Concentrate

The growth factor concentrate prepared and preserved from the aforesaid steps, or the composition described herein could be used in the cosmetic treatment to subject in need. In one embodiment, the growth factor concentrate could be applied as a serum on areas of treatment by rehydrating with 1:1 normal saline or be administered in form of powder directly on open moist wounds or ulcers.

Figure 2:
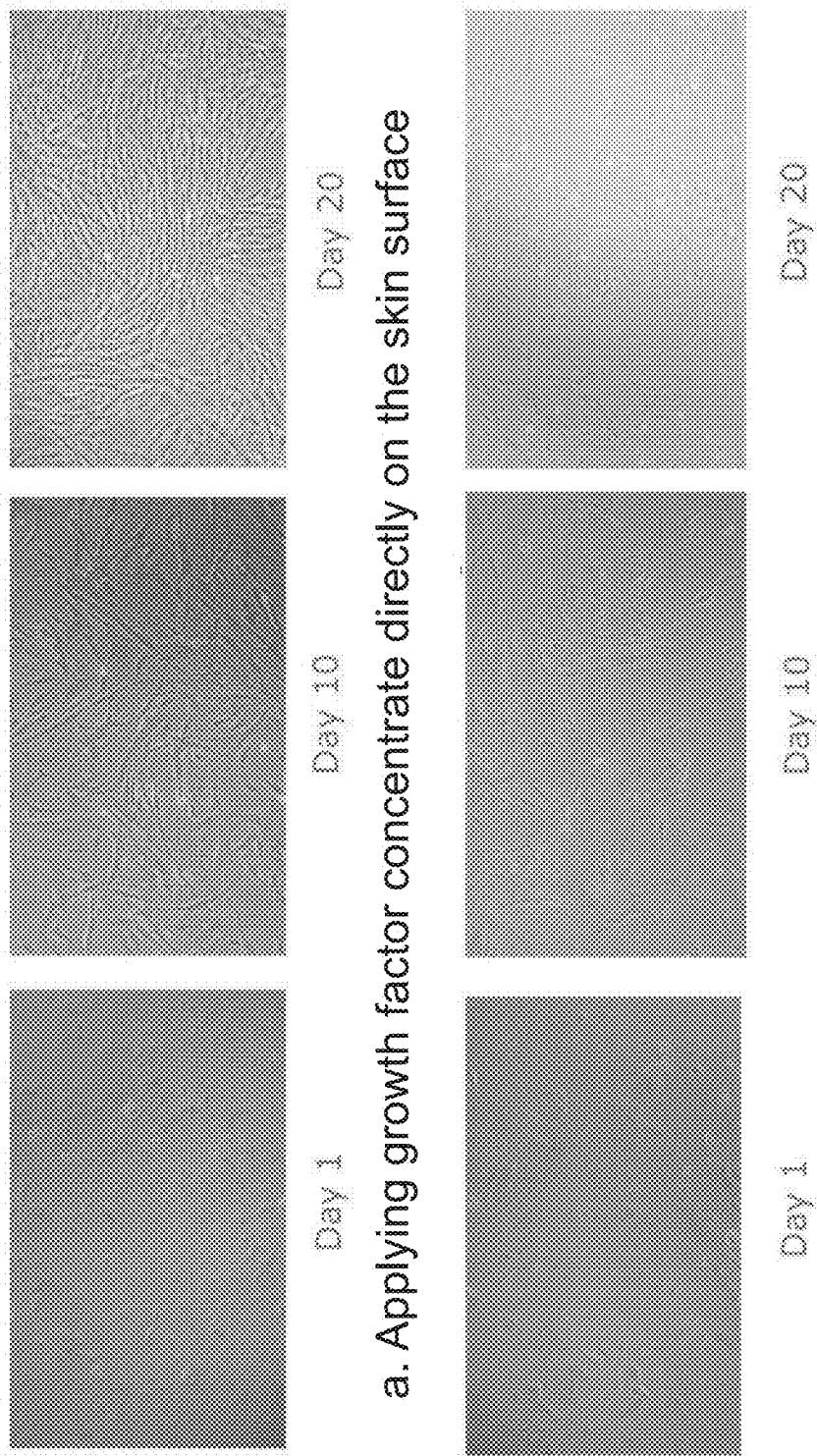
FIG. 2 shows the density of released growth factors under the epidermis of the subject in need of the growth factor concentrate applied by the method provided in the present invention and fresh growth factor applied by the injection.
Figure 3:
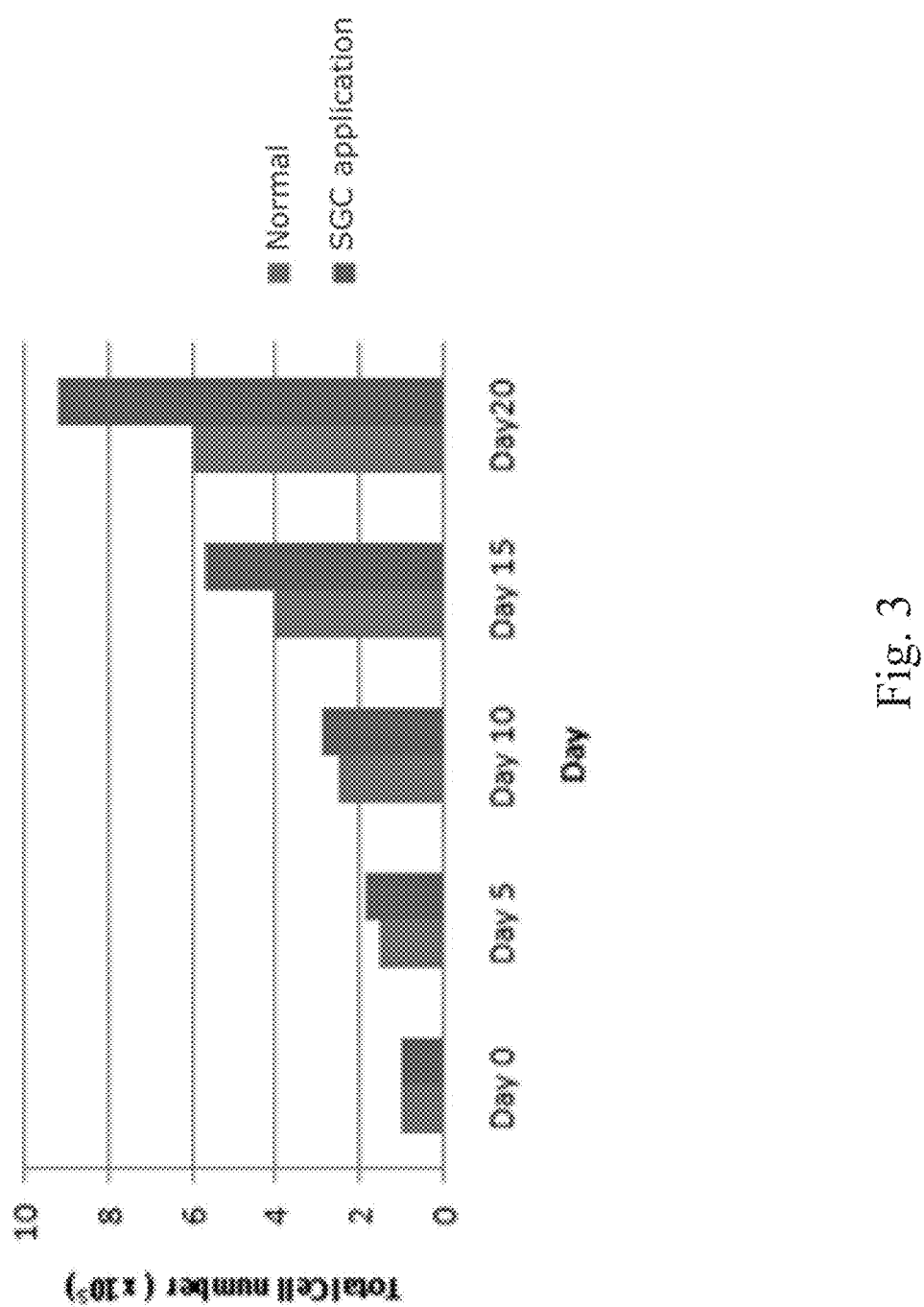
FIG. 3 shows the total cell number after the treatment of the growth factor concentrate provided in the present invention and a typical treatment using PRP.
Figure 4:
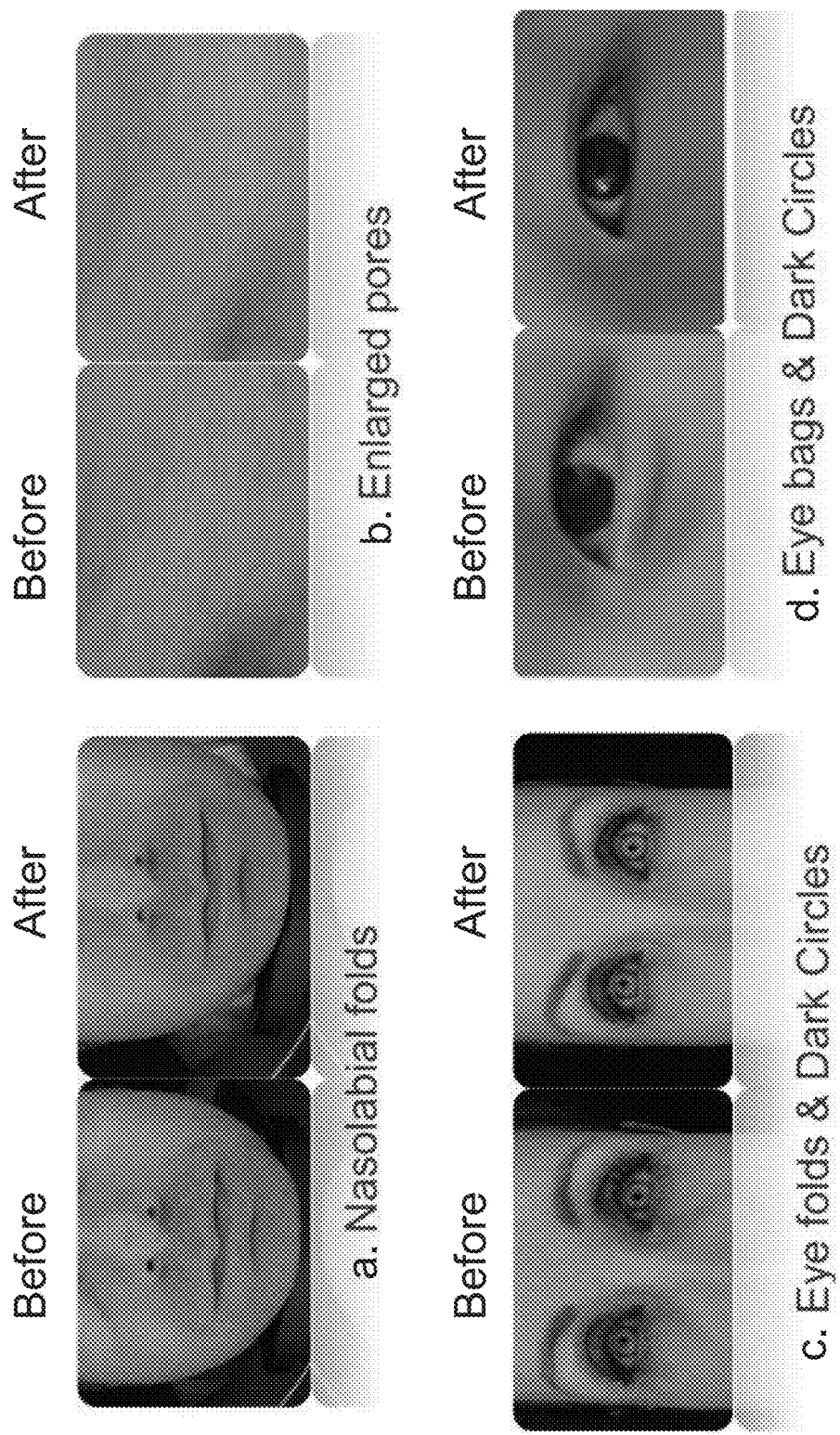
FIG. 4 shows results of the studies of the application of the growth factor concentrate provided in the present invention.

The results of the administration of the growth factor concentrate of the present invention in cosmetic treatment are shown in FIGS. 2, 3 and 4. FIG. 2 shows that there is a significant 10-time proliferation of cell number in applying the growth factor concentrate of the present invention directly on the skin surface as compared to that in applying fresh growth factor by injection. It shows that by applying the growth factor concentrate of the present invention directly on the skin surface, the be-treated skin area would have more released growth factors than that by applying fresh growth factor by injection.

FIG. 3 reveals the results of a study on the total cell number after the treatment of traditional growth factor and the growth factor concentrate of the present invention. The cell numbers were shown to increase by using both kinds of growth factors. However, after 20 days of the treatment, the number of cell by using the growth factor concentrate of the present invention was 1.5 times of that of using traditional growth factor.

FIG. 4 shows the results of actual clinical examples before and after the treatment using the growth factor concentrate of the present invention. It shows that the growth factor concentrate of the present invention could reduce nasolabial/eye folds, enlarged pores and eye bags; reduce dark spots and pigmentation; and improve the density, smoothness and firmness.

Applying on the Skin Surface

To improve the absorption rate of the growth factor concentrate during the treatment to the subject in need directly on the skin surface, bipolar radiofrequency (RF) technology is used in one embodiment of the present invention. Radiofrequency technology as a rejuvenation method is partially based on skin remodeling following a controlled injury and could be used for laser skin resurfacing, dermabrasion and deep chemical peels.

One embodiment of the present invention provides a method for rejuvenating skin comprising steps of:
a. cleaning the target area of the skin of the subject;
b. massaging the cleaned skin with a probe of a radiofrequency machine; and
c. applying a cosmetic composition comprising an effective amount of the growth factor concentrate of the present invention to the massaged skin.

In the same embodiment, a 10 $J/cm^3$ RF energy with 1.7 MHz is adapted. By massaging the skin before applying the growth factor concentrate, the growth factor concentrate can then easily permeate through the epidermis and the concentration thereof under the epidermis would be increased.

As used herein, the term "an effective amount" refers to a suitable amount that can affect on the result of an advantageous or desirable clinical or biochemical result. The effective amount may be administered once or more. The effective amount is also an amount suitable for temporarily alleviating, improving, stabilizing, reversing, slowing down, or delaying the progress of a disease state. In the present invention, the effective amount is the amount sufficient to rejuvenate the skin conditions, to reduce black spots in the skin, or to whiten the skin in a subject.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, the present invention is applicable on different kinds of growth factors including and not limited to Platelet Derived Growth Factor (PDGF), Transforming Growth Factor Beta (TGF-B), Insulin-like Growth Factor (IGF-1), Platelet Factor-4 (PF-4), Vascular Endothelial Growth Factor (VEGF), Epidermal Growth Factor (EGF), Hepatocyte Growth Factor (HGF), Bone Morphogenetic Proteins (BMPs) and Fibroblast Growth Factor (FGF).

EXAMPLES

Example 1 Preparation of Hematopoietic Extract (HE)/PRP Solution Collection Kit 1.1.1 Prepare a sample collection box,
1.1.2 And prepare 6 enrollment labels for each HE collection kit
1.1.3 In each collection box contains:
50 mL HE collection kit; 1×40 mL Blood collection tubes, 1×10 mL Blood Collection tube, 1× butterfly needle (21 G), 5× needle (20 G), 2× alcohol swaps, 1×50 mL syringe, 3×1 mL syringe, 3× short needle (30 G), 6× enrollment label (1+1 labels already on Blood collection tubes), corresponding HE storage enrollment form and blood collection instruction. 100 mL HE collection kit; 3×30 mL Blood collection tubes, 1×10 mL Blood Collection tube, 1× butterfly needle (21 G), 5× needle (20 G), 2× alcohol swaps, 2×50 mL syringe, 3×1 mL syringe, 3× short needle (30 G), 6× enrollment label (3+1 labels already on Blood collection tubes), corresponding HE storage enrollment form and blood collection instruction.

1.1.4 Check the expiry dates of each item.

1.1.5 Record the expiry dates and lot numbers of all items on the Collection kit preparation form, sign and check by another staff.

1.1.6 Mark the Enrollment number and earliest expiry date on the collection box and seal the box and stamp for quality check passed.

1.2 Collection of HE 1.2.1 Collect 50 mL or 100 mL peripheral whole blood by venipuncture, volume accords to the service enrollment. Fresh blood should be dispensed in blood tubes in the following order in 10 minutes, before the blood starts to clot:
a. For 50 mL blood collection place 10 mL in 14 mL blood tube (fill tube up to the labeled mark) and then 40 mL of blood each into the 40 mL blood tube (fill up to the labeled mark)
b. For 100 mL blood collection place 10 mL in 14 mL blood tube (fill tube up to the labeled mark) and then 30 mL each in three 50 mL blood tubes (fill tube up to the labeled mark)

1.2.2 Gently invert the blood tubes to mix the blood with the anticoagulant.

1.2.3 Label the Tubes with the date of blood collection and the name of the client.

1.2.4 The 10 mL blood tube is for first time HE injection, which can be discarded after. Use the 1 mL syringes provided for HE injection.

1.2.5 Keep the large blood tubes at temperature between 4-25° C. before collection by SCI currier within 12 hrs upon notification.

1.2.6 For Sample pickup procedures please see SCI-LB-SOP-015.

1.3 Sample Labeling of HE before lyophilization 1.3.1 Before the process, the sample should be assigned with a HE number. The format of the sample number should be HEYYYY-XXXX while YYYY is the year of the sample is being processed and XXXX is the number of case in the year.

1.3.2 HE label and PPP label containing the (1) HE number, (2) Processing start date (3) Best until date, 6 months after processing start date (4) Enrollment number and (5) Client's initials should be printed. Please note: The PPP label has the HE number in unicase to distinguish between HE and PPP samples.

1.3.3 For 50 mL blood sample print 27×HE labels and 6×PPP labels; for 100 mL blood sample print 48×HE labels and 9×PPP labels.

1.3.4 Use the printed labels to label each sample tube carefully and the HE Sample Processing Information Record (SCI-LB-022).

Example 2 Preparation of Growth Factor Concentrate Before Lyophilisation 1.4.1 Process the blood in HE isolator for 15 min, 20° C.

1.4.2 The blood components will be separated into layers by centrifugal force and HE layer will be separated in a collection bag.

1.4.3 The volume of the HE is usually less than 40% of the totally blood volume. Collect the HE from the blood tubes using a 20 mL syringe, measure the volume and record the volume onto the HE Sample Processing Information Record.

1.4.4 Transfer the HE into a fresh centrifuge tube, label the tube with HE label.

1.4.5 Prepare a prechilled lysing solution of 50 mM Tris, pH 7.4, 250 mM NaCl, 5 mM Haprine, 50 mM NaF, 1 mM $Na_3VO_4$, 1% Nonidet P40, 0.02% $NaN_3$.

1.4.6 According to the HE volume add lysing solution with anticoagulant then incubate on ice with vortexing in intervals.

1.4.7 After lysing add a tris based lyoprotectant. The ratio 3% lyoprotectant:HE is 1:10.

1.4.8 Then transfer the mixture in a suitable container and fast freeze in liquid nitrogen for a few minutes.

1.4.9 Thaw the mixture at 30° C. and then wash the mixture with saline and tris buffer for three times, until a product is achieved (QC tested for growth factor count and trace of additives).

1.4.10 Mix the product well by pippetting up and down for at least 3 times, and distribute the HE into eppendorff tubes at 1 mL per tube.

1.4.11 Label each tube individually with a sample label.

1.4.12 Draw a 1 mL sample from one of the eppendorf tubes for sterility test. Inoculate the sample into two broth bottles TAB and Clear-Thio at 0.5 mL each.

1.4.13 Count the total number of eppendorf tubes left after sampling and record in the HE Sample Processing Information Record.

1.4.14 Arrange the all tubes in 2-3 controlled rate freezing containers.

1.4.15 Store the HE in the freezing container at −55±5° C. freezer for at least 4 hours.

1.5 Storage of the Growth Factor Concentrate 1.5.1 The PPP will be used to rehydrate the HE after lyophilization.

1.5.2 It will be aliquoted into 15 mL centrifuge tubes, 3 mL in each tubes.

1.5.3 Draw 1 mL of PPP for sterility test by injecting the PPP into the same pair of Broth bottles.

1.5.4 Label the tubes with PPP label and store at −55±5° C. until use.

1.5.5 This frozen PPP can be kept up to 12 months.

Example 3 Lyophilisation of the Growth Factor Concentrate 1.6.1 Retrieve the frozen samples from −55±5° C.

1.6.2 In a safety cabinet, open the cap of the frozen sample.

1.6.3 Place the tubes and freezing container back into the −55±5° C. freezer for 15 min.

1.6.4 Pre-cool the freeze-drier cabinet to −50° C.

1.6.5 Retrieve samples from freezer and place them into the pre-cooled a glass beaker provided with the freeze dryer, start the vacuum pump and keep the pressure at about 1 Pa, leave the samples to dry for at least 5 hours or until they are completely dried.

1.6.6 Check if the samples are completely dried. Remove the samples from the freeze-dryer and immediately seal the tubes, store the tubes at 22-25° C. of humidity lower than 60%. This lyophilized Growth Factor Concentrate can be stored for 6 months according to SCI internal standard, but many study have soon efficacy of HE preserved using similar method can last up to 24 months.

Example 4 Rehydration of the Growth Factor Concentrate 1.7.1 Rehydration must be carried out on the appointed date of the Growth Factor Concentrate injection.
1.7.2 Retrieve Growth Factor Concentrate from −55±5° C. and thaw in 37° C. water bath, prepare a Growth Factor Concentrate solution by mixing PPP:water for injection at ratio 1:1.
1.7.3 Resuspend the lyophilized Growth Factor Concentrate in the solution prepared above at room temperature.
1.7.4 Gently shake the sample until is completely dissolved.
1.7.5 Use a 1 mL syringe to draw 1 mL of rehydrated plasma and attach with a 30 G needle.
1.7.6 Wrap the syringe with a sterile pouch and Label clearly with Growth Factor Concentrate Label.
1.7.7 This rehydrated Plasma should be stored and transported to the site of injection at 4-25° C. and must be used within 48 hours from rehydration.

What is claimed is:

1. A method of preparing a growth factor concentrate comprising steps of:
    extracting a whole blood sample from a subject, wherein platelet rich plasma with the growth factors are contained therein;
    obtaining the platelet rich plasma from the blood sample;
    stabilizing the platelet rich plasma by adding a Tris Buffer at 2% in volume to stabilize pH at 7 to avoid undesired fluctuations of pH value in temperature extremes of the following steps;
    decapsulating the growth factors from the platelets of the stabilized platelet rich plasma comprising: 1) lysing the stabilized platelet rich plasma with a lysing solution; 2) freezing the platelet rich plasma at a temperature between −50° C. and −60° C. for 5-30 minutes and thawing the platelet rich plasma at a temperature of 37° C. for 10-30 minutes; filtering out the decapsulated growth factors by a 0.2 μm cellulose acetate membrane; freeze-drying the filtered growth factors by freezing the filtered growth factors at a temperature between −50° C. and −60° C.' for at least 3 hours and lyophilizing the frozen growth factors at a temperature between −40° C. and −60° C. and at a pressure of about 0.01-0.18 millibar for at least 10 hours, wherein the freeze-dried growth factor concentrate has humidity of lower than 70%; and 3) repeat step 2) three more times; and preserving the freeze-dried growth factor concentrate at about 4° C.

2. The method of claim 1, wherein the lysing solution in the decapsulating step is NP-40 lysis buffer.

3. The method of claim 2, wherein the lysing solution further comprises an anticoagulant.

4. The method of claim 3, wherein the anticoagulant is selected from one consisting of heparin, warfarin, coumarin, dabigatran, rivarosaban, apixaban, edoxaban, sodium citrate and sodium calcium.

5. A method of preparing a growth factor concentrate comprising steps of:
    extracting a whole blood sample from a subject, wherein platelet rich plasma with the growth factors are contained therein;
    obtaining the platelet rich plasma from the blood sample;
    decapsulating and stabilizing the growth factors from the platelets rich plasma comprising: 1) lysing the platelet rich plasma with a lysing solution; 2) stabilizing the platelet rich plasma by adding a Tris Buffer at 2% in volume to stabilize pH at 7 to avoid undesired fluctuations of pH value in temperature extremes of the following steps; 3) freezing the platelet rich plasma at a temperature between −50° C. and −60° C. for 5-30 minutes and thawing the platelet rich plasma at a temperature of 37° C. for 10-30 minutes; filtering out the decapsulated growth factors by a 0.2 μm cellulose acetate membrane; freeze-drying the filtered growth factors by freezing the filtered growth factors at a temperature between −50° C. and −60° C. for at least 3 hours and lyophilizing the frozen growth factors at a temperature between −40° C. and −60° C. and at a pressure of about 0.01-0.18 millibar for at least 10 hours, wherein the freeze-dried growth factor concentrate has humidity of lower than 70%; and 4) repeat step 3) three more times; and preserving the freeze-dried growth factor concentrate at about 4° C.

6. The method of claim 5, wherein the lysing solution in the decapsulating step is NP-40 lysis buffer.

7. The method of claim 6, wherein the lysing solution further comprises an anticoagulant.

8. The method of claim 7, wherein the anticoagulant is selected from one consisting of heparin, warfarin, coumarin, dabigatran, rivarosaban, apixaban, edoxaban, sodium citrate and sodium calcium.

* * * * *